United States Patent
Tzomik et al.

(10) Patent No.: US 10,042,274 B2
(45) Date of Patent: Aug. 7, 2018

(54) PRIMER COMPOSITION AND METHOD

(71) Applicant: HP Indigo B.V., Amstelveen (NL)

(72) Inventors: Inna Tzomik, Modiin (IL); Hannoch Ron, Kadima (IL); Shani Maor, Tel Aviv (IL); Einat Glick, Nes Ziona (IL); Alexander Stolov, Nes Ziona (IL)

(73) Assignee: HP Indigo B.V., Amstelveen (NL)

( * ) Notice: Subject to any disclaimer, the term of this patent is extended or adjusted under 35 U.S.C. 154(b) by 0 days.

(21) Appl. No.: 15/522,285

(22) PCT Filed: Jan. 19, 2015

(86) PCT No.: PCT/EP2015/050867
§ 371 (c)(1),
(2) Date: Apr. 26, 2017

(87) PCT Pub. No.: WO2016/116129
PCT Pub. Date: Jul. 28, 2016

(65) Prior Publication Data
US 2017/0329244 A1  Nov. 16, 2017

(51) Int. Cl.
*G03G 21/00* (2006.01)
*G03G 7/00* (2006.01)
(Continued)

(52) U.S. Cl.
CPC ........... *G03G 7/0053* (2013.01); *G01N 21/64* (2013.01); *G01N 21/8422* (2013.01); *G03G 9/12* (2013.01); *G01N 2021/8427* (2013.01)

(58) Field of Classification Search
CPC .............................. G03G 9/12; G03G 7/0053
See application file for complete search history.

(56) References Cited

U.S. PATENT DOCUMENTS

| 3,235,560 A | 2/1966 | Kaveggia et al. |
| 3,772,199 A | 11/1973 | Tamai et al. |

(Continued)

FOREIGN PATENT DOCUMENTS

| EP | 1594011 | 11/2005 |
| EP | 1843212 | 10/2007 |

(Continued)

OTHER PUBLICATIONS

"SpecMetrix In-line Coating Measurement Systems Win 2014 ICE Asia Innovation Award", SpecMetrix, Business Wire, 2014, 2pgs, http://www.businesswire.com.

(Continued)

*Primary Examiner* — Peter L Vajda
(74) *Attorney, Agent, or Firm* — HP Inc. Patent Department

(57) ABSTRACT

A method for determining coat weight of a transparent primer coating for liquid electrophotographic printing processes is described, in which an optical brightening agent is added to an aqueous transparent primer composition in an amount of less than 0.1 wt. % based on the total solids content of the primer composition to produce a test composition, the test composition is applied onto a test substrate to produce a transparent primer coating, the fluorescence of the transparent primer coating is measured, and the coat weight of the transparent primer coating based on the fluorescence of the transparent primer coating is determined.

16 Claims, 1 Drawing Sheet

(51) Int. Cl.
*G03G 9/12* (2006.01)
*G01N 21/64* (2006.01)
*G01N 21/84* (2006.01)

(56) References Cited

U.S. PATENT DOCUMENTS

| | | | |
|---|---|---|---|
| 3,956,630 A * | 5/1976 | Mellows | G01G 9/00 250/252.1 |
| 6,566,024 B1 | 5/2003 | Bourdelais et al. | |
| 7,245,843 B2 | 7/2007 | Bessho | |
| 7,616,910 B2 | 11/2009 | Bessho | |
| 7,894,732 B2 | 2/2011 | Denton et al. | |
| 8,565,628 B2 | 10/2013 | Henderson | |
| 8,609,315 B2 | 12/2013 | Yoshida et al. | |
| 8,626,012 B2 | 1/2014 | Yoshioka | |
| 8,634,108 B2 | 1/2014 | Kojima et al. | |
| 8,656,528 B2 | 2/2014 | Perelman et al. | |
| 8,728,696 B2 | 5/2014 | Yamada et al. | |
| 8,749,845 B2 | 6/2014 | Kuo et al. | |
| 8,755,699 B2 | 6/2014 | Kuo et al. | |
| 8,760,719 B2 | 6/2014 | Tyagi et al. | |
| 8,781,353 B2 | 7/2014 | Regelsberger et al. | |
| 8,805,217 B2 | 8/2014 | Kuo et al. | |
| 2008/0233313 A1 | 9/2008 | Chatow et al. | |
| 2009/0104373 A1 | 4/2009 | Vanbesien et al. | |
| 2009/0238616 A1 | 9/2009 | Ciaschi | |
| 2009/0239174 A1 | 9/2009 | Inaba et al. | |
| 2010/0291474 A1 | 11/2010 | Baran, Jr. | |
| 2010/0330487 A1 | 12/2010 | Veregin et al. | |
| 2011/0002704 A1 | 1/2011 | Fujita | |
| 2011/0003245 A1 * | 1/2011 | Pohlt | G03G 9/13 430/115 |
| 2011/0007359 A1 | 1/2011 | Yamakawa et al. | |
| 2011/0212326 A1 | 9/2011 | Ettrich et al. | |
| 2011/0274896 A1 | 11/2011 | Krames et al. | |
| 2012/0201559 A1 | 8/2012 | Holland | |
| 2013/0259501 A1 | 10/2013 | Regelsberger et al. | |
| 2014/0341601 A1 | 11/2014 | Miyazaki | |

FOREIGN PATENT DOCUMENTS

| | | |
|---|---|---|
| WO | WO-96/31808 | 10/1996 |
| WO | WO-99/61955 | 12/1999 |
| WO | WO-01/88619 | 11/2001 |
| WO | WO-2007130559 | 11/2007 |
| WO | WO-2013043780 | 3/2013 |

OTHER PUBLICATIONS

"Spectra Phoenix II Measures the Thickness of Silicon Coating", Spectro, 2pgs http://www.spectro.com/pages/e/p060103.htm.
International Search Report and Written Opinion for International Application No. PCT/EP2015/050867 dated Sep. 23, 2015, 10 pages.

* cited by examiner

PRIMER COMPOSITION AND METHOD

BACKGROUND

Digital printing technologies, for example electrophotographic printing, involve creation of a printed image directly from digital data, for example using electronic layout and/or desktop publishing programs.

Electrophotographic printing techniques involve the formation of a latent image on a photoconductor surface mounted on an imaging plate. The latent image is developed using either a dry toner (a colorant mixed with a powder carrier) or a liquid ink (a suspension of a colorant in a liquid carrier). Liquid compositions used in liquid electrophotography are generally comprised of pigment- or dye-based thermoplastic resin particles suspended in a non-conducting liquid carrier, generally a saturated hydrocarbon. The toner or ink generally adheres to the substrate surface with little penetration into the substrate.

Adhesion of the thermoplastic resin particles of the liquid electrophotographic print composition to certain print substrates can be improved by deposition of a primer composition onto the print substrate before the liquid electrophotographic print composition is printed.

DETAILED DESCRIPTION

It is to be understood that this disclosure is not limited to the particular materials and process steps disclosed herein because such materials and process steps may vary somewhat. It is also to be understood that the terminology used herein is used for the purpose of describing particular examples only. The terms are not intended to be limiting because the scope of the present disclosure is intended to be limited only by the appended claims and equivalents thereof.

It is noted that, as used in this specification and the appended claims, the singular forms "a," "an," and "the" include plural referents unless the context clearly dictates otherwise.

As used herein, "liquid electrophotographic composition" generally refers to a liquid composition having a carrier liquid, and a polymer resin suitable for printing in an electrophotographic composition. In some examples, the liquid electrophotographic composition is a print composition and further comprises a pigment or colorant. A liquid electrophotographic composition may further comprise a mixture of a variety of different agents or additives, including without limitation, surfactants, organic solvents and co-solvents, charge control agents, viscosity modifiers, sequestering agents, stabilizing agents, and anti-coagulation agents.

Unless stated otherwise, "primer composition" or "aqueous transparent primer composition" as described herein is to be understood to mean a water-based composition which does not contain any pigment and so appears transparent to the naked eye under normal light when applied on a substrate. The primer compositions described herein may be referred to as non-pigmented primer compositions, or as transparent primer compositions, which are to be understood as being interchangeable.

As used herein, "carrier liquid" or "liquid vehicle" refers to the fluid in which the polymer resin of a liquid electrophotographic composition can be dispersed. Such a carrier liquid can be formulated for electrophotographic printing so that the electrophotographic composition has a viscosity and conductivity for such printing.

As used herein, "co-solvent" refers to any solvent, including organic solvents, present in the primer composition or in the liquid electrophotographic composition.

As used herein, "optical brightening agent" generally refers to a molecule which absorbs UV light between 380 and 270 nm and emits light at 420 to 500 nm, i.e. a fluorescent molecule. Fluorescent molecules are those which absorb light or other electromagnetic radiation and emit longer wavelength electromagnetic radiation. Such optical brightening agents are known and are used to increase the perception of brightness or whiteness of papers, textiles, plastics and other materials. As used herein, "optical brightening agent" is to be understood as referring to the class of fluorescent molecules which are colourless (i.e. white), or only weakly coloured in the solid state or in solution, and which are distinct to fluorescent dyes which appear coloured to the naked eye.

As used herein, the fluorescence profile of the optical brightening agent refers to the difference between the fluorescence emission of a substrate and the fluorescence emission of a test composition as described herein printed on that same substrate.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, the term "substantially" or "substantial" refers to the complete or nearly complete extent or degree of an action, characteristic, property, state, structure, item, or result.

As used herein, references to "molecular weight" are to weight-averaged molecular weight.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 wt % to about 5 wt %" should be interpreted to include not only the explicitly recited values of about 1 wt % to about 5 wt %, but also include individual values and sub-ranges within the indicated range. Thus, included in this numerical range are individual values such as 2, 3.5, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

Measurement of coat thickness or coat weight of pigmented electrophotographic inks for quality control and process efficiency purposes is possible based on the color density of the printed ink. However, since transparent primer compositions are non-pigmented, it is not possible to determine coat thickness or coat weight of these transparent compositions in this manner.

It has been recognised that inclusion of an optical brightening agent as described herein into a transparent or non-pigmented aqueous primer composition allows an in-line determination of thickness or coat weight of the printed primer composition based on the fluorescence profile of the composition comprising the optical brightening agent. In one example, the optical brightening agent described herein is added to a transparent or non-pigmented aqueous primer composition for the purposes of calibrating a coating apparatus so that a desired coat weight of the transparent primer composition is printed. Once the apparatus has been calibrated, the transparent or non-pigmented aqueous primer composition can be coated onto a print substrate without inclusion of the optical brightening agent.

Thus, the present disclosure is directed to methods of determining coat weight of a primer coating; methods of printing and to primer compositions. That being understood, it is noted that when discussing the present methods and associated compositions, each of these discussions can be considered applicable to each of these examples, whether or not they are explicitly discussed in the context of that example.

The present disclosure provides a method for determining coat weight of a transparent primer coating for liquid electrophotographic printing processes, comprising:
 (i) adding to an aqueous transparent primer composition an optical brightening agent in an amount of less than 0.1 wt. % based on the total solids content of the primer composition to produce a test composition;
 (ii) applying the test composition onto a test substrate to produce the transparent primer coating;
 (iii) measuring the fluorescence of the transparent primer coating; and
 (iv) determining the coat weight of the transparent primer coating based on the fluorescence of the transparent primer coating.

The aqueous transparent primer composition may be a non-pigmented or colourless composition. The optical brightening agent may be a non-pigmented or colourless optical brightening agent.

Additionally the present disclosure provides a method of printing, comprising determining coat weight of a printed primer composition according to the methods described herein, adjusting a parameter of the coating process based on the determined coat weight, applying the aqueous primer composition onto a print substrate to produce a primed print substrate, and printing a liquid electrophotographic composition onto the primed print substrate.

The present methods and compositions allow for an inline determination of the coat weight of a printed, transparent primer composition based on the fluorescence profile of the optical brightening agent, and calibration of the coating or priming apparatus.

Figure 1:
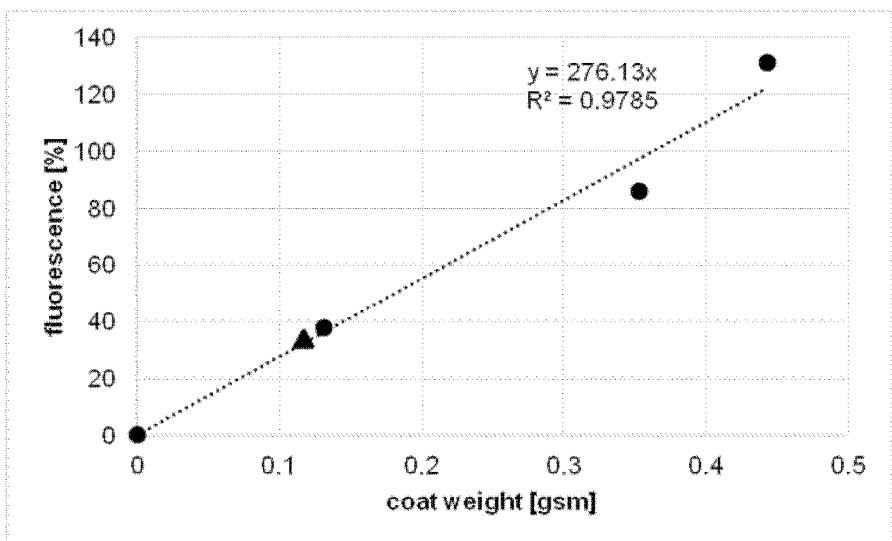
FIG. 1 shows the correlation between the coat weight of a transparent primer composition according to Example 1 and measured fluorescence.

Described herein are methods of determining coat weight of a printed transparent primer composition of the type used for priming substrates for liquid electrophotographic printing, and methods of printing, for example by first calibrating a primer coating apparatus on the basis of the determined coat weight using fluorescence measurements. The coating apparatus may be any coating apparatus suited for providing primer coatings on print substrates.

The methods described herein use a test composition comprising an aqueous transparent primer composition into which an optical brightening agent has been added.

Aqueous transparent primer compositions generally comprise adhesion enhancing materials to provide better adhesion of a liquid electrophotographic ink composition to a print substrate. For example, liquid electrophotographic ink compositions do not generally adhere well to plastics substrates such as BOPP (biaxially oriented polypropylene) and PET (polyethylene terephthalate).

The adhesion enhancing materials can be polymeric materials which bond to the print substrate with greater efficiency than the polymeric resins present in the liquid electrophotographic ink compositions.

In one example, the polymeric material is present in the aqueous primer composition in an amount of at least 2.0 wt % based on the total solids of the composition. In one example, the polymeric material is present in the aqueous primer composition in an amount of at least 3.0 wt % based on the total solids of the composition. In one example, the polymeric material is present in the aqueous primer composition in an amount of at least 4.0 wt % based on the total solids of the composition. In one example, the polymeric material is present in the aqueous primer composition in an amount of at least 5.0 wt % based on the total solids of the composition. In one example, the polymeric material is present in the aqueous primer composition in an amount of at least 6.0 wt % based on the total solids of the composition. In one example, the polymeric material is present in the aqueous primer composition in an amount of at least 7.0 wt % based on the total solids of the composition. In one example, the polymeric material is present in the aqueous primer composition in an amount of at least 8.0 wt % based on the total solids of the composition. In one example, the polymeric material is present in the aqueous primer composition in an amount of at least 9.0 wt % based on the total solids of the composition. In one example, the polymeric material is present in the aqueous primer composition in an amount of at least 10 wt % based on the total solids of the composition. In one example, the polymeric material is present in the aqueous primer composition in an amount of at least 20 wt % based on the total solids of the composition. In one example, the polymeric material is present in the aqueous primer composition in an amount of at least 30 wt % based on the total solids of the composition. In one example, the polymeric material is present in the aqueous primer composition in an amount of at least 40 wt % based on the total solids of the composition. In one example, the polymeric material is present in the aqueous primer composition in an amount of at least 50 wt % based on the total solids of the composition. In one example, the polymeric material is present in the aqueous primer composition in an amount of at least 60 wt % based on the total solids of the composition. In one example, the polymeric material is present in the aqueous primer composition in an amount of at least 70 wt % based on the total solids of the composition. In one example, the polymeric material is present in the aqueous primer composition in an amount of about 80 wt % based on the total solids of the composition.

In one example, the polymeric material is present in the aqueous primer composition in an amount of less than 80 wt % based on the total solids of the composition. In one example, the polymeric material is present in the aqueous primer composition in an amount of less than 70 wt % based on the total solids of the composition. In one example, the polymeric material is present in the aqueous primer composition in an amount of less than 60 wt % based on the total solids of the composition. In one example, the polymeric material is present in the aqueous primer composition in an amount of less than 50 wt % based on the total solids of the composition. In one example, the polymeric material is present in the aqueous primer composition in an amount of less than 40 wt % based on the total solids of the composition. In one example, the polymeric material is present in the aqueous primer composition in an amount of less than 30 wt % based on the total solids of the composition. In one example, the polymeric material is present in the aqueous primer composition in an amount of less than 20 wt % based on the total solids of the composition. In one example, the polymeric material is present in the aqueous primer composition in an amount of less than 10 wt % based on the total solids of the composition. In one example, the polymeric material is present in the aqueous primer composition in an amount of less than 9.0 wt % based on the total solids of the composition. In one example, the polymeric material is present in the aqueous primer composition in an amount of less than 8.0 wt % based on the total solids of the composition. In one example, the polymeric material is present in the aqueous primer composition in an amount of less than 7.0 wt % based on the total solids of the composition. In one example, the polymeric material is present in the aqueous primer composition in an amount of less than 6.0 wt % based on the total solids of the composition. In one example, the polymeric material is present in the aqueous primer composition in an amount of less than 5.0 wt % based on the total solids of the composition. In one example, the polymeric material is present in the aqueous primer composition in an amount of less than 4.0 wt % based on the total solids of the composition. In one example, the polymeric material is present in the aqueous primer composition in an amount of less than 3.0 wt % based on the total solids of the composition. In one example, the polymeric material is present in the aqueous primer composition in an amount of about 2.0 wt % based on the total solids of the composition.

In one example, the aqueous transparent primer composition comprises a polymeric material comprising one or more of a polyethyleneimine, a polyurethane, a polyamide, a polycarbodiimide, a hydrogenated hydrocarbon rosin or rosin ester, and a copolymer of an alkylene monomer and a monomer selected from acrylic acid and methacrylic acid.

The polymeric material can include, but is not limited to, a polyethylenimine polymer (e.g., having a weight-averaged molecular weight of about 25,000 to 700,000), polyethylene-co-acrylic acid polymer (ammonium salt) (e.g., having a molecular weight of about 10,000 to 30,000), thermoplastic polyamide, amine terminated polyamide, methylated polyethylenimine polymer, and combinations thereof.

In one example, the polyethylenimine polymer has a molecular weight of about 25,000 or 700,000. The polymer can be about 1 to 25, about 2 to 10 and about 2.5 to 5 weight percent of the primer. In general, having greater weight percent of polymer in the primer composition is advantageous for adhesion. In one example, the polyethylenimine is about 2.5 to 10% weight percent of the primer composition.

In an example, the primer composition contains either about 2-8% of a polyethylenimine having a molecular weight of about 25,000 (Lupasol WF) or about 2-5% a polyethylenimine having a molecular weight of about 700,000 (Lupasol P).

In an example, the primer composition comprises a polyurethane polymer which comprises from about 55 to 75% of the coating, and contains about 30 to 35% total solids. Suitable polyurethane dispersions are commercially available from NeoResins under the designation NeoRez® R-600, or NeoRez® FP-967-D. Other suitable aliphatic polyurethane dispersions include NeoRez® R-610 (available from NeoResins), NeoRez® R-605 XP (available from DSM) and Kamthane S-1801 (available from Kamsons).

Other suitable aliphatic polyurethane dispersions are commercially available from BASF under the designations Epotal® FLX 3621 (an amorphous polyurethane dispersion), Epotal® P 350 (an elastomeric polyether polyurethane dispersion), Emuldur® 381 A (an elastomeric polyester polyurethane dispersion), Luphen® D 207 (an elastomeric polyester-polyurethane dispersion), Luphen® D 259 (an elastomeric polyether-polyurethane dispersion), and Luphen® 585 (an elastomeric polyester-polyurethane dispersion); from Lubrizol under the designations Sancure® 2170 and 2175; and from Baxenden Chemicals under the designations Witcobond® 781 and 373-04.

In an example, the primer composition comprises a polyamide. In the present description and unless otherwise indicated, polyamides refer to a polymer containing amides groups in which the repeating units in the molecular main chain are linked together by amide groups. Examples of such polymers include for instance Macromelt® 6239 from Henkel, Germany.

In an example, the primer composition comprises a polycarbodiimide, or a reactive polycarbodiimide component, such as those described in U.S. Pat. No. 8,778,482 B2. Examples of commercial compositions including suitable polycarbodiimide components which can be used as primer compositions include but are not limited to those known under the following trademarks: SV-02 Carbodilite®, Ucarink® XL-29SE® (Union Carbide), EX-5558® (from Stahl Holland BV), Carbodilite® E02, E04, V02, V04 (manufactured by Nisshinbo Holdings Inc.), NK Assist CI® (manufactured by Nicca Chemical Co., Ltd.), and the like.

In an example, the primer composition comprises a hydrogenated hydrocarbon rosin or rosin ester. The hydrogenated hydrocarbon rosin or rosin ester should preferably have a ring and ball softening point in the range of from about 70° C. to 105° C. Suitable rosins for use include natural rosins, which typically include mixtures of resin acids or resin acid derivatives and esters. Examples of resin acids include tricyclic diterpenoids, including pimaranes such as pimaric acid, sandaracopimaric acid, isopimacric acid, delta 8-isopimaric acid, 7, 15-pimaradienoic acid, and delta 8-pimaric acid, abietanes such as abietic acid, levopimaric acid, palustric acid, neoabietic acid, dehydroabietic acid, dihydroabietic acid, and tetrahydroabietic acid. Examples of resin acid derivatives include, but are not limited to, rosin esters (such as glycerol ester of rosin acid and pentaerythritol ester of rosin acid), rosin fumarics, rosin maleics, rosin phenolics, fortified rosins, and hydrogenated rosins.

Suitable natural rosins include, but are not limited to, oleoresins, tall oil, wood or gum rosins from tree and plant extrudates, wood extracts, and some tackifying resins. Wood extracts include, but are not limited to, terpenoids including polymers made from monoterpenoids (such as α-pinene, β-pinene, and dipentenes), sesquiterpenoids, diterpenoids (including labdanes), sesterpenoids, triterpenoids, tetraterpenoids, and polyterpenoids.

One example of a hydrogenated rosin for use in the primer composition is a thermoplastic acidic resin which is produced by hydrogenating wood rosin. An example of such a hydrogenated rosin is Foral® AX rosin, available from Eastman, which is suitable for indirect food contact applications.

In an example, the primer composition comprises a copolymer of an alkylene monomer and a monomer selected from acrylic acid and methacrylic acid. The ethylene acrylic acid copolymer may comprise from about 65 to 95 wt % ethylene and from about 5 to 35 wt % acrylic or methacrylic acid. The copolymer may have a number average molecular weight of about 2,000 to 180,000. The copolymer is preferably prepared as a dispersion by heating the solid polymer with a water phase in a pressure reactor in the presence of a base such as ammonia such that the base reacts with the acid groups on the polymer, and upon melting, the polymer forms a colloidal dispersion. The primer composition preferably contains from about 30 to 45 wt % of the copolymer dispersion containing 35% by weight total solids. A suitable ethylene acrylic acid dispersion for use in the present methods is commercially available from Michelman under the designation Michem®Prime 4990R.E. Further examples of ethylene-acrylic acid copolymers include Honeywell AC®51 80 EAA and the Primacor® family from Dow Corning.

The primer composition may further comprise an anionic wax emulsion. The anionic wax emulsion may comprise a polyethylene wax emulsion, a carnauba wax emulsion, a high density polyethylene wax emulsion, or a combination thereof. In one example, a combination of wax emulsions enhances non-blocking properties over the use of a single wax or no wax without any negative impact on toner adhesion. One example of a polyethylene wax emulsion is commercially available from Michelman, Inc. under the designation ME61335P (solids content of 34.5 to 35.5%). Suitable carnauba wax emulsions are also available from Michelman, Inc. under the designations Michem® Lube 193 (solids content of 24.5 to 25.5%) or Michem® Emulsion 1270 (24.5 to 25.5%). A suitable high density polyethylene wax emulsion is available from Michelman, Inc. under the designation Michem® Emulsion D800 (solids content of 40.0 to 44.0%).

In addition, the primer composition can include a water-miscible co-solvent. Solvents that belong to the class of "linear alcohols" can be included in the primer composition. Alkane-diols and -triols can be used, for example, those with the hydroxyl groups present at or near only one end of the molecule. Some examples include, but are not limited to: 1,2-butanediol, 1,2-pentanediol, 1,2-hexanediol, 1,2,3-hexanetriol, 1,2-heptanediol, and 1,2-octanediol.

Such co-solvents are amphiphilic in nature, i.e. they have a hydrophobic end and a hydrophilic end. This amphiphilic nature allows the solvent to wet hydrophobic surfaces well, and thus penetrate and spread rapidly on paper. Thus, the co-solvent may also be referred to as a wetting agent. In one example, the co-solvent includes 1,2-hexanediol. The "co-solvent" can be about 0 to 40, about 2 to 20, and about 4 to 10 weight percent of the primer composition. In one example, the primer composition comprises from about 0 to 5 weight percent of co-solvent.

Also, the primer composition can include, but is not limited to, a surfactant and water. The surfactant can include, but is not limited to, anionic surfactants, non-ionic surfactants, zwitterionic surfactants, cationic surfactants, and the like. In an example, nonionic acetylenic glycol surfactants with HLB (hydrophile-lipophile balance) of 4-5 can be used. The surfactant can be about 0 to 5, about 0.1 to 1 and about 0.2 to 0.5 weight percent of the primer. Water constitutes the balance of the weight percent of the primer composition.

The primer composition can have a pH of about 4 to 11, about 7 to 10, and about 8 to 9.5. The pH of the primer composition can be adjusted down by a mono-protic strong acid (e.g., hydrochloric acid, nitric acid, or methanesulfonic acid). Conversely, the pH of the primer composition can be adjusted up by a strong base (e.g., sodium hydroxide and potassium hydroxide). The pH adjuster can be added at anytime during preparation of the primer composition. The amount of primer disposed on the substrate can be about 0.1 gsm to 10 gsm, about 1 gsm to 5 gsm, and about 1.5 gsm to 3 gsm.

In one example, the primer composition can be a commercially available primer composition and can include, but is not limited to, Sapphire™, Topaz™, Digiprime™, Emicote™, and Curecoat.

The test composition includes an optical brightening agent (OBA). Optical brightening agents are typically used to improve whiteness and/or brightness of a media. An OBA absorbs ultraviolet light and re-emits blue light and so is a fluorescent compound. The blue light is added to the reflected light of the media. The media appears less green and/or yellow because more blue light is reflected.

An OBA is also commonly referred to as a fluorescence whitening agent (FWA). It has been recognised that inclusion of an optical brightening agent into a liquid electrophotographic composition allows an inline determination of the coat weight or thickness of the printed composition based on the fluorescence profile of the optical brightening agent. References in this disclosure to the fluorescence profile of the optical brightening agent are to the difference between the fluorescence emission of the unprinted substrate and the fluorescence of a primer composition as described herein printed on the substrate.

Basic classes of OBA that can be used in the test composition include triazine-stilbenes, coumarins, imidazolines, diazoles, triazoles, benzoxazolines, and biphenyl-stilbenes. Different OBAs are commercially available from a number of sources, including BASF Corporation Clariant Corporation, and the like. Tinopal® SFP is the trade name of an OBA commercially available from BASF Corporation. Leucophor® NS is the trade name of an anionic OBA commercially available from Clariant Corporation. Other examples of OBAs include Megawhite DT, Megawhite 2B, Megawhite WHN, Megawhite DMX (from Meghmani Dyes and Intermediates Ltd, India), Uvitex OB.

In one example, the test composition described herein is used to determine coat weight of a transparent primer composition to be printed. The OBA is present in the test composition in an amount sufficient to allow determination of a fluorescence profile once the composition has been printed.

The OBA can be present in the test composition in an amount of at least 0.01 wt % based on the total solids of the composition. In another example, the OBA can be present in the test composition in an amount of at least 0.05 wt % based on the total solids of the composition. In another example, the OBA can be present in the test composition in an amount of at least 0.06 wt % based on the total solids of the composition. In another example, the OBA can be present in the test composition in an amount of at least 0.07 wt % based on the total solids of the composition. In another example, the OBA can be present in the test composition in an amount of at least 0.08 wt % based on the total solids of the composition. In another example, the OBA can be present in the test composition in an amount of at least 0.09 wt % based on the total solids of the composition. In another example, the OBA can be present in the test composition in an amount of at about 0.1 wt % based on the total solids of the composition.

In another example, the OBA can be present in the test composition in an amount less than 0.1 wt % based on the total solids of the composition. In another example, the OBA can be present in the test composition in an amount less than 0.09 wt % based on the total solids of the composition. In another example, the OBA can be present in the test composition in an amount less than 0.08 wt % based on the total solids of the composition. In another example, the OBA can be present in the test composition in an amount less than 0.07 wt % based on the total solids of the composition. In another example, the OBA can be present in the test composition in an amount less than 0.06 wt % based on the total solids of the composition. In another example, the OBA can be present in the test composition in an amount less than 0.05 wt % based on the total solids of the composition. In another example, the OBA can be present in the test composition in an amount of about 0.01 wt % based on the total solids of the composition.

The test composition may also contain a fluorescence adjuvant. The fluorescence adjuvant increases the visible blue light emissions significantly and so enhances the fluorescence profile of the optical brightening agent in the printed composition. The fluorescence adjuvant may be an organic polyol. Examples of suitable polyols include high molecular weight polyethylene glycol or polyvinyl alcohol. Other examples of organic polyols which can be used as a fluorescence adjuvant include maltose monohydrate, sucrose, dextrin and sorbitol.

The test composition may contain a fluorescence adjuvant in an amount of at least 20 wt % of the total amount of solids present in the composition. The test composition may contain a fluorescence adjuvant in an amount of at least 25 wt % of the total amount of solids present in the composition. The test composition may contain a fluorescence adjuvant in an amount of at least 30 wt % of the total amount of solids present in the composition. The test composition may contain a fluorescence adjuvant in an amount of at least 40 wt % of the total amount of solids present in the composition. The test composition may contain a fluorescence adjuvant in an amount of about 50 wt % of the total amount of solids present in the composition.

The test composition may contain a fluorescence adjuvant in an amount of less than 50 wt % of the total amount of solids present in the composition. The test composition may contain a fluorescence adjuvant in an amount of less than 40 wt % of the total amount of solids present in the composition. The test composition may contain a fluorescence adjuvant in an amount of less than 30 wt % of the total amount of solids present in the composition. The test composition may contain a fluorescence adjuvant in an amount of less than 25 wt % of the total amount of solids present in the composition. The test composition may contain a fluorescence adjuvant in an amount of about 20 wt % of the total amount of solids present in the composition.

The methods of determining coat weight of a primer coating as described herein comprise a step of adding to an aqueous transparent primer composition an optical brightening agent in an amount of less than 0.1 wt. % based on the total solids content of the primer composition to produce a test composition. The optical brightening agent may be added at room temperature, or at any temperature required to dissolve the optical brightening agent, and mixed. Since most optical brightening agents are water soluble, the adding can take place at room temperature.

Prior to applying the primer coating to a test substrate, the substrate can be surface treated by a flame treatment or corona discharge treatment. This surface treatment can improve adhesion of the primer coating and the overlying electrophotographic ink composition and can be applied either in-line or off-line.

The test composition can be applied to polymeric substrates which are printed using HP Indigo WS6600 or WS6000 Digital Presses. These presses are designed to print onto labels for packaging, including wine labels, flexible packaging, sleeves, and folding cartons. Such digital presses include an optional in-line priming unit which allows the press to apply primer to uncoated substrates in-line and dry the primer just prior to printing. Thus, the presses are capable of priming and printing substrates in a single pass.

Alternatively, the test composition may be applied to a substrate offline by conventional flexographic or gravure coating techniques. One example of a suitable off-line coating apparatus is the Digicoat coater from ABG International. In one example, the test composition can be applied onto a test substrate according to the standard operating parameters of any of the aforementioned machines to produce a transparent primer coating the fluorescence of which is to be measured.

The test substrate may be any substrate which is suitable for an electrophotographic printing process and which may benefit from having a primer coating before printing.

In one example, the test substrate is a plastic-based material including, but not limited to, polyolefins such as polyethylene, HDPE and LDPE, Linear low density polyethylene (LLDPE), fluted polyolefins such as fluted polyethylene available under the name COROPLAST, oriented polypropylene OPP and BOPP, oriented Nylon CPA, casted polypropylene CPP, polycarbonate, acrylonitrile-butadiene-styrene (ABS), PET, PETG, rigid vinyl, pressure sensitive vinyl, vinyl films, acrylics, top-coated and print-treated polyesters, polystyrene, polyethylene coated card stock, PVC, expanded foam PVC such as Sintra®, Celtec™, and foam board, metalized polymeric films.

In another embodiment example, the test substrate is a lignocellulosic based substrate including a paper or any lignocellulose-containing material.

The method of determining coat weight also comprises measuring the fluorescence of the printed composition. The fluorescent radiation can be quantified using any fluorometer. A suitable fluorometer is the PerkinElmer LS45 luminescence spectrometer. To avoid any experimental variation, the fluorescent intensity may be normalised against a photochemically fluorescent stable standard. One example of such a standard is USFS-205-020 from Labsphere (NH, USA).

In one example, the fluorescence measurement of the printed transparent primer composition and/or the test substrate may be carried out in-line with the printing step. In this context, "in-line" will be understood as meaning that the printed article is received by the fluorometer directly after leaving the printing or coating apparatus. In one example, the fluorescence measurement is carried out immediately after the primer coating has been formed. This ensures that there can be no deterioration in the fluorescence profile of the optical brightening agent and coating containing the same.

Measurement of the fluorescence of the printed composition and the test substrate allows the determination of the coat weight based on the fluorescence profiles so obtained. In one example, this determination may be carried out by reference to a previously generated calibration curve of coat weight versus normalised fluorescence intensity. The calibration curve may be generated by printing different numbers of layers of the transparent test composition onto a test substrate at various test patches (for example 10, 15, 20 and 25), measuring the fluorescence as described previously at each point, determining coat weight gravimetrically after removal of the printed compositions from the substrate and correlating this with the measured fluorescence.

The present disclosure also relates to a method of printing, comprising performing the method of determining coat weight described previously, and adjusting a parameter of the coating process based the determined coat weight. For example, if the method of determining coat weight reveals that the coating apparatus has printed too much composition and the coat weight is greater than desired or intended, a parameter of the coating process can be adjusted to ensure that less test composition is transferred to the print substrate.

In one example, adjusting a coating parameter comprises adjusting the amount of the test composition applied onto the test substrate. In one example, adjusting a coating parameter comprises adjusting a dosing parameter, a coating temperature, a coating pressure, or any combination thereof.

In one example, a dosing parameter is adjusted to transfer less or more of the test composition to the test substrate. Transferring more or less of the test composition will result in more or less of the composition being applied onto the test substrate. For example, if it was identified that a coat weight was 5% above target weight determined according to the methods described herein, a dosing parameter can be adjusted to deliver 5% less composition to the coating apparatus. In one example, a coating parameter may be adjusted by selecting a roller weight for a given coating apparatus.

In one example, a coating or roller temperature is adjusted to transfer more or less of the test composition to the test substrate. In one example, a coating or roller pressure is adjusted to transfer more or less of the test composition to the test substrate.

In one example, the steps of determining a coat weight and adjusting a coating parameter may be repeated until a desired coat weight is reproducibly achieved, before the step of applying the transparent primer composition onto the print substrate and printing an electrophotographic composition onto the primed substrate. The step of applying the transparent aqueous primer composition to the print substrate to produce a primed print substrate comprises operating the coating apparatus according to the last set of operating parameters applied during the calibration steps, but applying the aqueous transparent primer composition in place of the test composition (comprising the primer composition and the optical brightening agent).

The method of printing comprises a step of printing a liquid electrophotographic composition onto the primed print substrate. The liquid electrophotographic composition will typically comprise a polymer resin dispersed in a carrier liquid, and optionally a colorant or pigment particle encapsulated in the polymer resin. Suitable compositions comprise polymer resins including copolymers of ethylene and acrylic acid or methacrylic acid dispersed in a hydrocarbon or paraffinic carrier fluid such as Isopar. Examples of suitable liquid electrophotographic compositions include the HP series of ElectroInks. The step of printing a liquid electrophotographic composition can be carried out on any electrophotographic printing press, for example the HP Indigo presses described previously.

The present disclosure also provides a method of manufacturing an aqueous transparent primer composition as described herein, comprising mixing an aqueous primer composition, or components thereof, and an optical brightening agent. In one example, the method comprises mixing a polymeric material comprising one or more of a polyethyleneimine, a polyurethane, a polyamide, a polycarbodiimide, a hydrogenated hydrocarbon rosin or rosin ester, and a copolymer of an alkylene monomer and a monomer selected from acrylic acid and methacrylic acid, an optical brightening agent, optionally a co-solvent, one or more additives as previously described herein and water for sufficient time until the composition is suitable for use as a coating composition.

Example

The following example is to be understood as being only exemplary or illustrative of the application of the principles of the present disclosure. Numerous modifications and alternative compositions and methods may be devised by those skilled in the art without departing from the spirit and scope of the present disclosure. Thus, this example should not be considered as limitations of the present disclosure, but is merely in place to teach how to make and use compositions of the present disclosure.

Fluorescence was determined using a PerkinElmer® LS45 luminescence spectrometer. Excitation wavelength was 350 nm while fluorescence was measured at 450 nm. As mentioned above, fluorescent intensity is measured in RFU (relative fluorescent units). In order to exclude the effect of the fluorometer, a photochemically fluorescent stable standard was used as a reference. All the fluorescence values reported are relative to the fluorescence values of the standard measured before each experiment. The standard used was USFS-205-020 from Labsphere (NH, USA).

The primer composition was the commercially available DigiPrime® 050 from Michelman (10% w/w solids), a recommended primer for HP's Indigo ElectroInks®. To this was added 0.1 wt % of Uvitex® OB (from BASF), which is used as an OBA for textile whitening.

The resultant test composition was applied on 20 micron thick BOPP film (uncoated, from Dor Films) using a Digicoat coater from ABG International at a speed of 35 m/min. The thickness of the test composition was controlled by varying the Anilox roller used in the coater. Low coat weight was achieved using a 400×60×20 Anilox roller, medium coat weight was achieved using a 300×60×30 Anilox roller and a 200×60×40 Anilox roller produced the highest coat weight.

The BOPP was treated in-line by a corona (400 W) prior to coating. A roll was produced using each roller and analyzed. Coated BOPP was passed through a drier oven at 80° C. Five samples of 25 cm$^2$ were taken from each roll. The fluorescence from each sample was measured at 20 different spots. The weight of each sample was determined before and after removal of the primer from the samples for determining the coat weight. The dried primer was removed by rinsing the sample with hot water followed by cold water, while rubbing the sample using a special lint free textile cloth (Polynit polyester Knit wipes from Contec®, China). The weight of the sample was determined after drying 5 min in an oven at 60° C. The coat weight and the fluorescence of the different primer coat weights are shown in Table 1.

TABLE 1

Fluorescence and coat weight of primer coatings deposited by different Anilox rollers

| | Roller | | |
|---|---|---|---|
| | 400 × 60 × 20 low | 300 × 60 × 30 mid | 200 × 60 × 40 high |
| fluorescence [%] | 37.9 | 86.0 | 131.0 |
| stdv | 0.018 | 0.007 | 0.007 |
| coat weight [gsm] | 0.132 | 0.353 | 0.443 |
| stdv | 0.018 | 0.007 | 0.007 |

The fluorescence was calculated according to equation 1, in which "ink" refers to the printed primer composition and "background" refers to the test substrate:

$$\text{Reported fluorescence Intensity[\%]} = \frac{(\text{Fluorescence ink} - \text{Fluorescence background})}{\text{Fluorescence Labsphere reference}} * 100 \quad \text{Equation 1}$$

A calibration curve relating coat weight to fluorescence measurement is shown in FIG. 1 (round dots).

In addition to the calibration curve a separate independent coating experiment was conducted using low coat weight Anilox roller where a test composition comprising DigiPrime® 050 from Michelman (10% w/w solids) and 0.1% of Uvitex® OB was coated on BOPP (20 micron uncoated film from Dor Films). The fluorescence and the coat weight were determined using the same procedure as described above. The coat weight and the fluorescence are in full correlation with the calibration curve in FIG. 1 (triangle dot).

Figure 2:
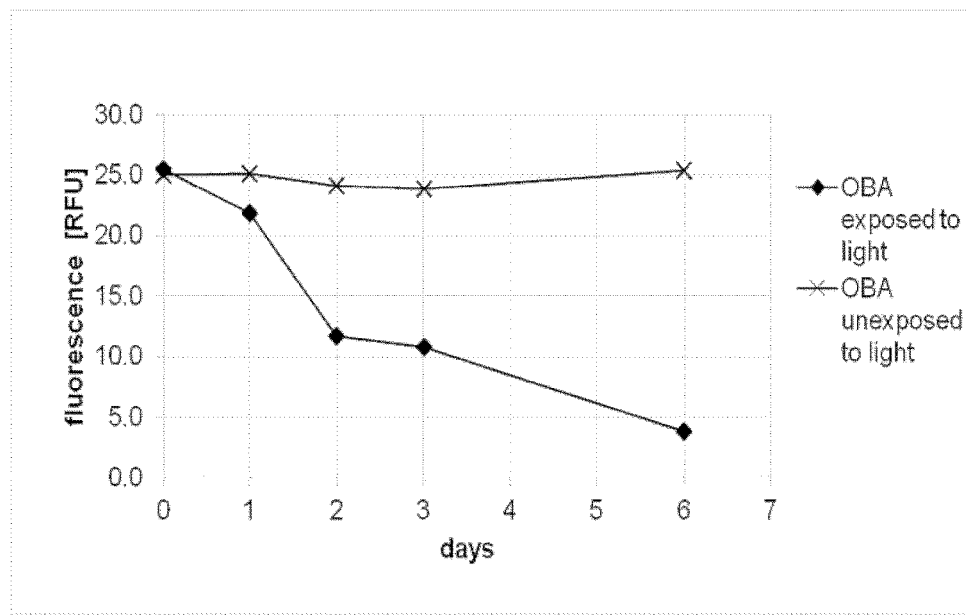
FIG. 2 shows the effect of time on the fluorescence intensity of a primer coating containing an optical brightening agent.

Stability of the fluorescent primer coated layers was explored. Decreasing fluorescence was observed with the time when the coated layers were exposed to light (diamonds). As is shown in FIG. 2, decreasing fluorescence of exposed layers occurred after a few hours. Layers not exposed to light have stable fluorescence for at least 48 hours (crosses). Determination of primer coat weight using the disclosed method is therefore reproducible and accurate if the coating composition containing the OBA is protected from light before coating and the fluorescence of the coated substrate is determined immediately after coating.

While the present disclosure has been described with reference to certain embodiments, those skilled in the art will appreciate that various modifications, changes, omissions, and substitutions can be made without departing from the spirit of the disclosure. It is intended, therefore, that the disclosure be limited only by the scope of the following claims. The features of any dependent claim can be combined with the features of any of the other dependent claims, and any independent claim.

The invention claimed is:

1. A method for determining coat weight of a transparent primer coating for liquid electrophotographic printing processes, comprising:
   (i) adding to an aqueous transparent primer composition an optical brightening agent in an amount of less than 0.1 wt. % based on the total solids content of the primer composition to produce a test composition that includes a balance of water;
   (ii) applying the test composition onto a test substrate to produce the transparent primer coating;
   (iii) measuring the fluorescence of the transparent primer coating; and
   (iv) determining the coat weight of the transparent primer coating based on the fluorescence of the transparent primer coating.

2. The method of claim 1, wherein the fluorescence of the transparent primer coating is measured directly after the transparent primer coating is produced.

3. The method of claim 1, wherein the test composition is a transparent or non-pigmented liquid electrophotographic composition.

4. The method of claim 1, wherein the optical brightening agent is a colourless optical brightening agent.

5. The method of claim 1, wherein the optical brightening agent is a fluorophore.

6. The method of claim 1, wherein the optical brightening agent comprises one or more of a triazine stilbene and derivatives thereof, a biphenyl stilbene and derivatives thereof, a coumarin and derivatives thereof, a benzoxazoline and derivatives thereof, a diazole and derivatives thereof, an imidazoline and derivatives thereof, or mixtures thereof.

7. The method of claim 1, wherein the coat weight of the transparent primer coating is directly proportional to the fluorescence of the transparent primer coating.

8. A method of printing, comprising:
   performing the method of claim 1;
   adjusting a parameter of the coating process based on the determined coat weight;
   applying the aqueous primer composition onto a print substrate to produce a primed print substrate; and
   printing a liquid electrophotographic composition onto the primed print substrate.

9. The method of claim 8, wherein adjusting the parameter of the coating process comprises adjusting the amount of the test composition printed onto the print substrate.

10. The method of claim 8, wherein adjusting the parameter of the coating process comprises adjusting a dosing parameter, a coating temperature, a coating pressure, or any combination thereof.

11. The method of claim 8, wherein the steps of determining the coat weight and adjusting the parameter of the coating process are repeated before printing the transparent primer composition onto the print substrate.

12. An aqueous transparent primer composition for priming a print substrate for a liquid electrophotographic printing process, the composition comprising:
   a polymeric material comprising one or more of a polyethyleneimine, a polyurethane, a polyamide, a polycarbodiimide, a hydrogenated hydrocarbon rosin or rosin ester, and a copolymer of an alkylene monomer and a monomer selected from acrylic acid and methacrylic acid;
   an optical brightening agent in an amount of less than 0.1 wt. % based on the total solids content of the primer composition; and
   a balance of water.

13. The composition of claim 12, wherein the optical brightening agent is a colourless optical brightening agent.

14. The composition of claim 12, wherein the optical brightening agent is a fluorophore.

15. The composition of claim 12, wherein the optical brightening agent comprises one or more of a triazine stilbene and derivatives thereof, a biphenyl stilbene and derivatives thereof, a coumarin and derivatives thereof, a benzoxazoline and derivatives thereof, a diazole and derivatives thereof, an imidazoline and derivatives thereof, or mixtures thereof.

16. The method of claim 1, wherein the test substrate is a plastic substrate selected from the group consisting of biaxially oriented polypropylene (BOPP) and polyethylene terephthalate (PET).

* * * * *